United States Patent [19]

Haber et al.

[11] Patent Number: 5,599,351
[45] Date of Patent: Feb. 4, 1997

[54] SCALPELS HAVING PERMANENT BLADE RETRACTION

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 163,910

[22] Filed: Dec. 8, 1993

[51] Int. Cl.$^6$ .................................................. A61B 17/32
[52] U.S. Cl. ............................ 606/167; 30/2; 30/151
[58] Field of Search ............................ 606/166, 167, 606/170, 172, 181, 182, 185; 30/2, 151, 162, 164, 220, 286, 335; 128/751

[56] References Cited

U.S. PATENT DOCUMENTS

| | | |
|---|---|---|
| 6,240 | 5/1849 | Ives . |
| 2,823,677 | 2/1958 | Hein . |
| 4,157,086 | 6/1979 | Maiorano et al. . |
| 4,825,545 | 5/1989 | Chase et al. . |
| 5,071,426 | 12/1991 | Dolgin et al. . |
| 5,201,748 | 4/1993 | Newman et al. ........................ 606/167 |
| 5,207,696 | 5/1993 | Matwijcow . |
| 5,254,128 | 10/1993 | Mesa . |
| 5,292,329 | 3/1994 | Werner . |
| 5,309,641 | 5/1994 | Wonderley et al. . |
| 5,330,492 | 7/1994 | Haugen . |
| 5,330,493 | 7/1994 | Haining ................................... 606/167 |
| 5,342,379 | 8/1994 | Volinsky .................................. 606/167 |
| 5,344,424 | 9/1994 | Roberts et al. .......................... 606/167 |

FOREIGN PATENT DOCUMENTS

0555196A1  1/1993  European Pat. Off. .
WO91/03984  4/1991  WIPO .

*Primary Examiner*—Stephen C. Pellegrino
*Assistant Examiner*—William W. Lewis
*Attorney, Agent, or Firm*—Townsend and Townsend and Crew

[57] ABSTRACT

Scalpel constructions are shown in which shipping of the scalpel occurs with the blade retracted, surgeon usage enables exposure of the scalpel blade from required cutting during surgery, and finally and upon completed use of the scalpel, one-way retraction of the scalpel into a "sharp-safe" blade covering disposition can occur. Thereafter, upon scalpel discard, the cutting edge of the scalpel is safely shielded and inhibited from further intentional or inadvertent cutting. A first design includes scalpel reciprocation along a handle against a detent for shipping with the blade within the handle, use with the blade exposed from the handle, and one-way retraction into the handle immediately prior to discard. A second design includes a handle folding across the scalpel body with a sleeve having a first position for covering the blade during shipping, a second position for holding the blade extended and exposed for surgery, and a third position for permanently locking about the scalpel blade after use. A third design includes a spring loaded scalpel normally producing blade retraction with the blade releasing to and from a protected position with provision made for locking the blade within the housing after use is completed. A fourth design includes a scalpel covered with a removable sheath having a hinge in the plane of the handle which is held in the extended position by a handle retained portion of the sheath. By sliding the sheath away from the hinge, the blade may be placed within a handle latch with the cutting edge of the blade permanently covered.

5 Claims, 7 Drawing Sheets

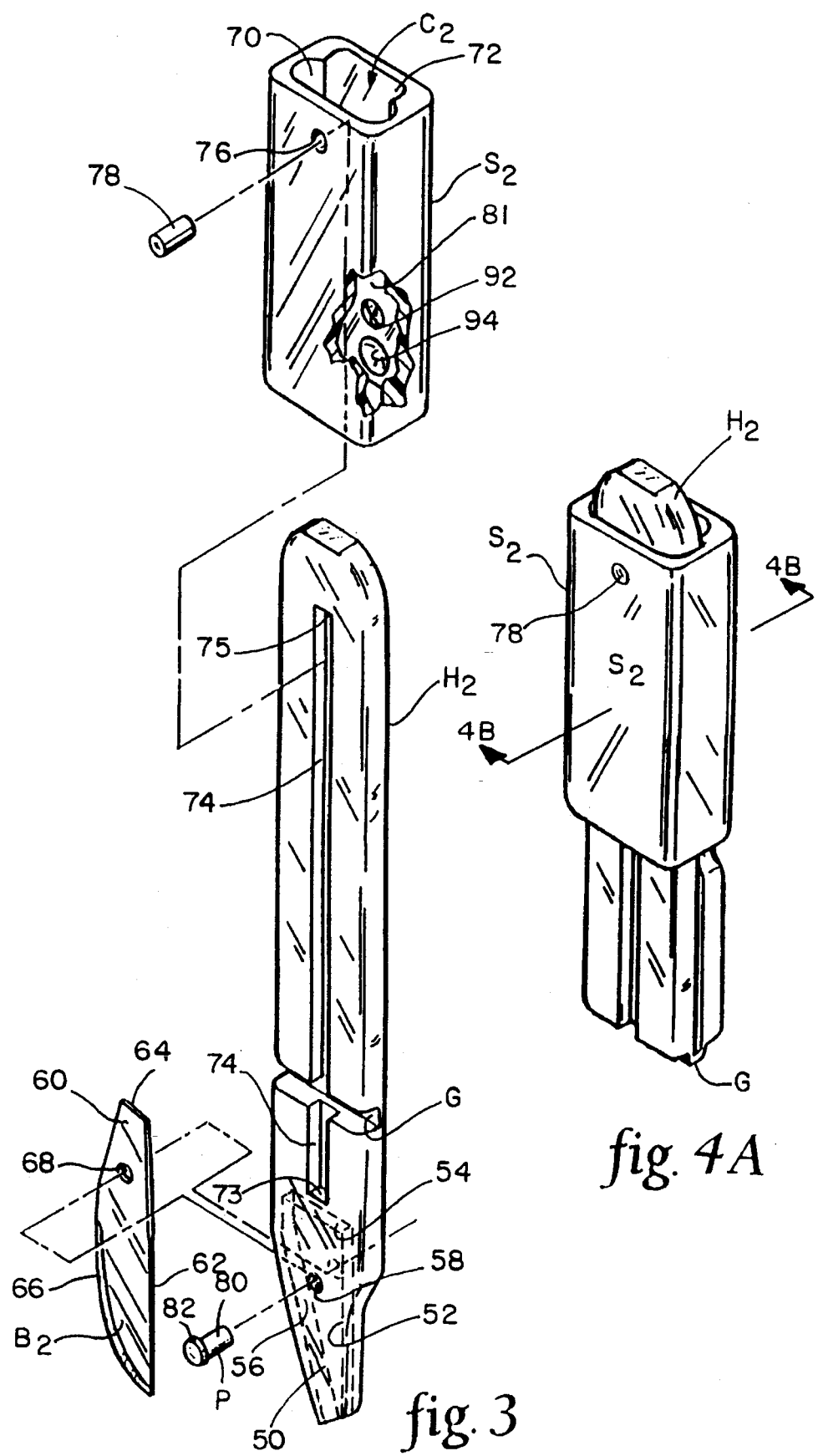

SCALPELS HAVING PERMANENT BLADE RETRACTION

This invention relates to scalpels. More particularly, scalpel constructions are shown which enable a scalpel when utilized to have its cutting edge retracted to shielded "sharp-safe" position and locked in that shielded position to avoid after use infection of others, especially by diseases transmitted in blood.

BACKGROUND OF THE INVENTION

Hepatitis-B, acquired immune deficiency syndrome (AIDS) and other blood carried diseases now require sanitary disposal of all articles contaminated with blood during normal usage. Perhaps the most singularly dangerous procedure exposing personnel to acquiring such blood transmitted diseases is surgery—especially if the subject of the surgery has a blood disease. Since the required time for detection of such diseases is not present where emergency procedures are required, it must be presumed that all patients are infected. Since scalpels cut flesh and flesh bleeds, scalpels are presumed to be, and are, extremely hazardous.

Because of such blood carried diseases, such scalpels must never inadvertently be re-used. Further, and once use occurs of a scalpel, it must be discarded in a disposition where the cutting edge is covered. The blade must not be exposed where further inadvertent cutting can occur—such as the puncturing of trash containers or the cutting of those handling trash.

Accordingly, it is the object of this invention to disclose scalpel constructions where the scalpel blade can be permanently retracted to a "sharp-safe" disposition after use.

SUMMARY OF THE INVENTION

Scalpel constructions are shown in which shipping of the scalpel occurs with the blade retracted, surgeon usage enables exposure of the scalpel blade from required cutting during surgery, and finally and upon completed use of the scalpel, one-way retraction of the scalpel into a "sharp-safe" blade covering disposition can occur. Thereafter, upon scalpel discard, the cutting edge of the scalpel is safely shielded and inhibited from further intentional or inadvertent cutting. A first design includes scalpel reciprocation along a handle against a detent for shipping with the blade within the handle, use with the blade exposed from the handle, and one-way retraction into the handle immediately prior to discard. A second design includes a handle folding across the scalpel body with a sleeve having a first position for covering the blade during shipping, a second position for holding the blade extended and exposed for surgery, and a third position for permanently locking about the scalpel blade after use. A third design includes a spring loaded scalpel normally producing blade retraction with the blade releasing to and from a protected position with provision made for locking the blade within the housing after use is completed. A fourth design includes a scalpel covered with a removable sheath having a hinge in the plane of the handle which is held in the extended position by a handle retained portion of the sheath. By sliding the sheath away from the hinge, the blade may be placed within a handle latch with the cutting edge of the blade permanently covered.

BRIEF DESCRIPTION OF THE DRAWINGS

FIG. 3 is an exploded isometric view of scalpel components illustrating a second embodiment with a folding scalpel handle and attached blade and a reciprocating sleeve for shielding the scalpel blade during shipment, holding the scalpel blade co-linearly and rigid during surgery, and permanently covering the scalpel blade after surgery and prior to discard;

FIG. 4A is a perspective view of the scalpel of FIG. 3 with the blade stored within the sleeve;

DESCRIPTION OF THE PREFERRED EMBODIMENT

Figure 1:
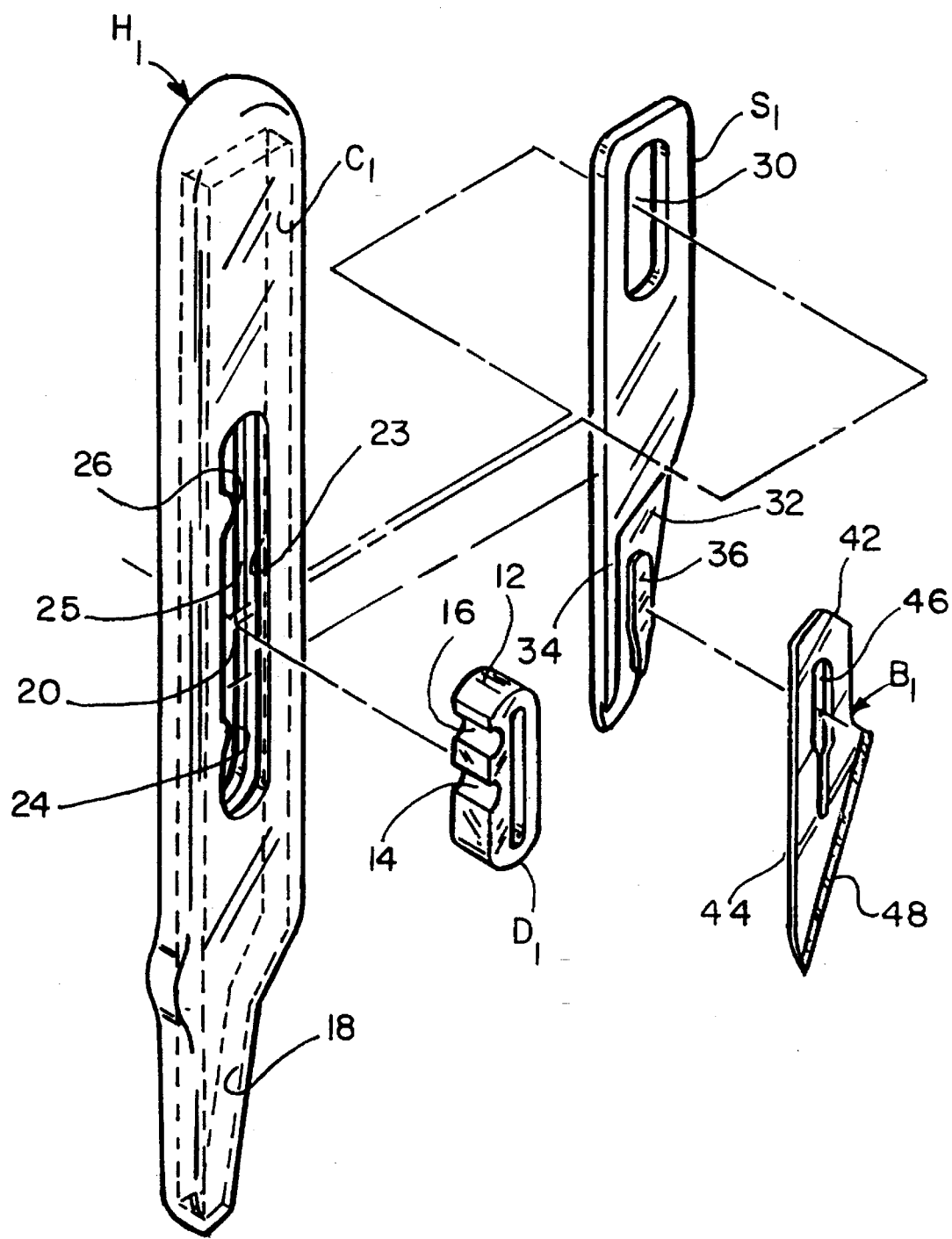
FIG. 1 is an exploded isometric view of scalpel components of a first embodiment illustrating respectively the scalpel handle, scalpel slider and blade, and a female detent mechanism for interacting with the slider and blade.

Referring to FIG. 1, handle $H_1$ is illustrated with a slider $S_1$ for holding blade $B_1$ in telescoping relation for sliding and out of a cavity $C_1$ defined within the handle. A detent $D_1$ having locking female detent 14 and releasable female detent 16 for co-action with lower and upper male detents 24, 26 in slot 20 exposing the interior of cavity $C_1$ is used to manipulate blade $B_1$. It will be observed that upper male detent 26 exceeds in size lower male detent 24. This construction will become important when permanent retraction of blade $B_1$ is required.

Handle $H_1$ is of hollow construction and defines a hollow rectilinear interior cavity $C_1$ having three openings. The first opening is a blade protrusion opening 18. Blade $B_1$ moves in and out of this opening. The second two side handle openings 23, 25 are formed at slot 20. These are the respective openings through which detent $D_1$ is manipulated for moving blade $B_1$.

Blade slider $S_1$ includes a detent receiving aperture 30 for receiving detent $D_1$. At the lower end, blade slider $S_1$ includes a half depth cavity 32 having a central key 36 and a side blade hold ridge 34.

Blade $B_1$ includes a blade body 42 with a central keyway 46 and a retaining edge 44. The blade includes a cutting edge 48 which must be stored upon shipping, extended for use, and permanently retracted to a sharp-safe disposition after use.

The assembly of the scalpel is easily understood. Slider $S_1$ has blade $B_1$ fitted with central key 36 to central keyway 46 with retaining edge 44 bearing against side blade holding ridge 34. In this partially assembled disposition, slider $S_1$ and blade $B_1$ are inserted to cavity $C_1$ in handle $H_1$. When such insertion occurs, the respective sides of cavity $C_1$ will maintain blade $B_1$ seated within slider $S_1$. There remains the requirement of locking slider $S_1$ interior of cavity $C_1$.

When slider $S_1$ is inserted interior of handle $H_1$, detent receiving aperture 30 registers to slot 20. Detent $D_1$ is inserted through one side handle opening 23 or 25. Insertion occurs until a detent key 12 registers to detent receiving aperture 30. This effectively locks slider $S_1$ and blade $B_1$ interior of handle $H_1$.

There now remains the explanation of the scalpel operation.

Figure 2C:
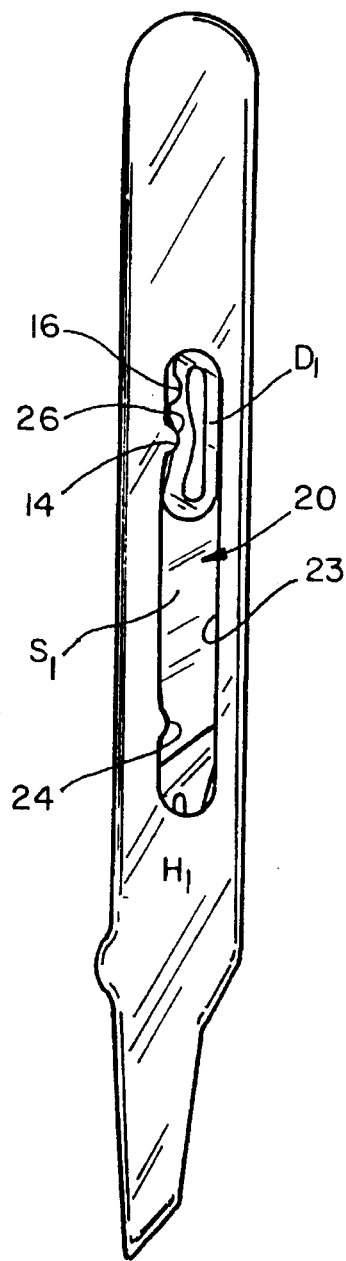
FIG. 2A, 2B and 2C are respective side elevations with FIG. 2A illustrating the scalpel in the disposition for shipping, FIG. 2B illustrating the scalpel with the blade exposed for surgery, and FIG. 2C illustrating the scalpel after surgery with the blade permanently retracted.
Figure 2B:
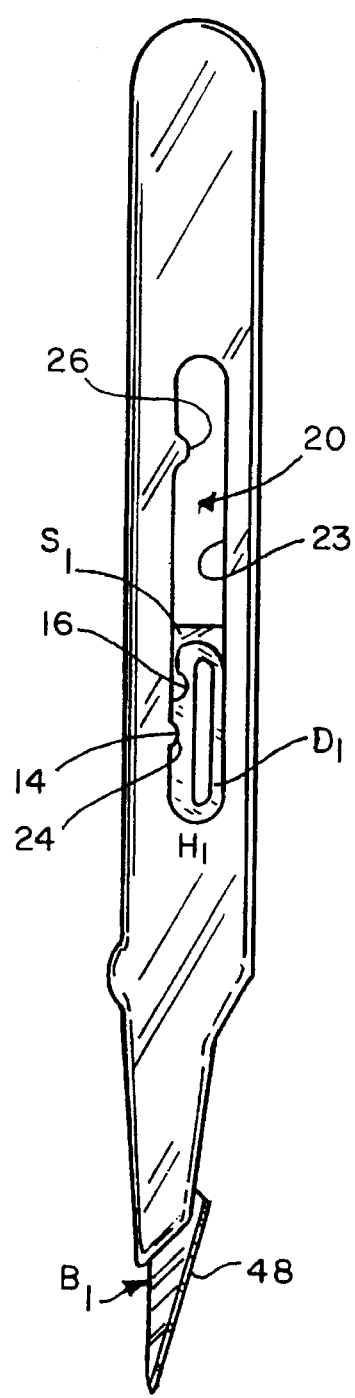
Figure 2A:
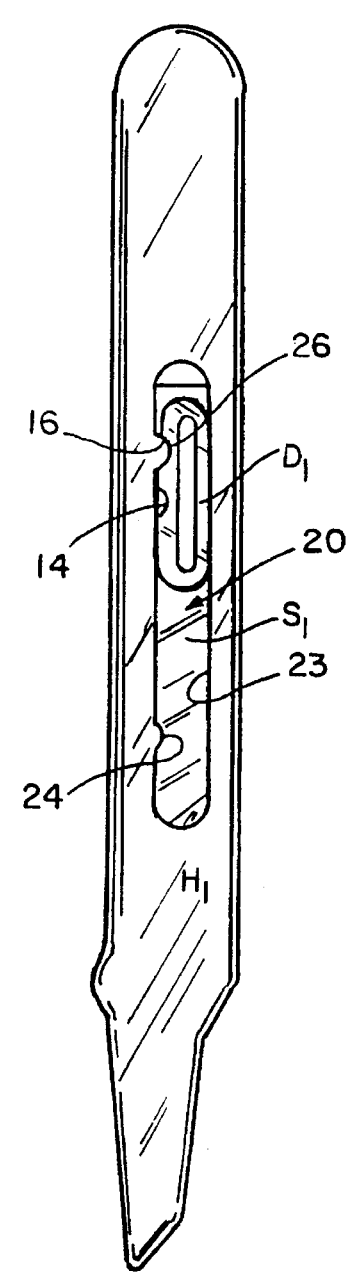

FIG. 2A illustrates the scalpel in the shipping disposition. Upper male detent 26 engages releasable female detent 16. This holds blade $B_1$ interior of handle $H_1$. Because female detent 16 is releasable, it enables pressure on detent $D_1$ to release slider $S_1$ with the slider moving generally downward. This movement occurs when the surgeon's hand overcomes the detent engagement and causes blade $B_1$ to protrude from cavity $C_1$ at blade protrusion opening 18 (See FIGS. 1 and 2B).

Use of the scalpel occurs with the disposition of blade $B_1$ with cutting edge 48 exposed. When use is completed, detent $D_1$ is moved upward by the surgeon for retraction of blade $B_1$. Such upward movement continues past that detent engagement of releasable female detent 16 with upper male detent 26 to engagement of locking female detent 14 with upper male detent 26.

This locking is illustrated with respect to FIG. 2C. Remembering that upper male detent 26 in the sides of slot 20 exceeded the dimension of lower male detent 24, it will be seen that deformation of detent $D_1$ occurs. This deformation permanently locks blade slider $S_1$ and blade $B_1$ interior of handle $H_1$. Further inadvertent cutting of blade $B_1$ is prevented.

Figure 4B:
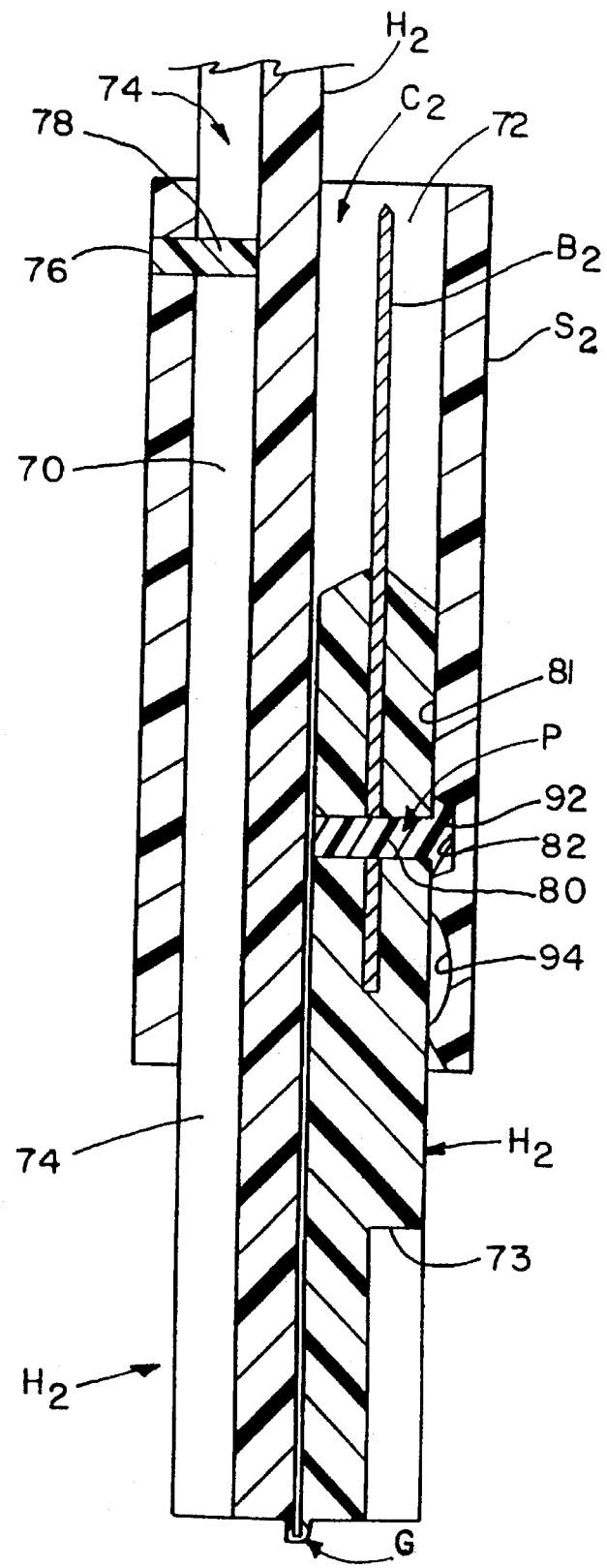
FIG. 4B is a side elevation section of the assembled scalpel of FIG. 3 in the disposition of FIG. 4A with the sleeve moved to permanently shield the blade prior to discard with an adjacent female detent being show which is utilized for holding the sleeve during shipping and releasing the blade for surgery.

A second embodiment of this invention can now be set forth with respect to FIGS. 3, 4A and 4B.

Referring to FIG. 3, handle $H_2$ includes a hinge G. Hinge G is located immediately above a blade securing cavity 50. Blade securing cavity 50 includes side edge 52, upper edge 54, and blade protrusion side 56. Pin hole 58 extends across both sides of handle $H_2$ at blade securing cavity 50.

Construction of blade $B_2$ is easier to understand. Blade body 60 includes blade side edge 62, blade upper edge 64, and cutting edge 66. Blade body 60 has blade body aperture 68 which registers with pin hole 58 in handle $H_2$.

A slider $S_2$ is provided. Slider $S_2$ includes central slider cavity $C_2$ having handle cavity section 70 and blade cavity section 72. It will be noted that handle cavity section 70 is broader than blade cavity section 72. This enables sliding of slider $S_2$ along the outside surface of handle $H_2$ exposing blade cavity section 72 for sharp-safe capture of blade $B_2$.

When the scalpel is assembled, it is required that slider $S_2$ key to the side of handle $H_2$ and not become disengaged from its sliding relation on the handle $H_2$. This being the case, handle $H_2$ is provided with a side handle slot 74 which extends across hinge G. This slot 74 receives a slider pin 78 protruding into handle cavity section 70 of slider $S_2$ and held by pin aperture 76 so as to be integral to slider $S_2$.

Ignoring for the moment the interior construction of slider $S_2$, assembly can be easily understood. Slider $S_2$ is placed over handle $H_2$ at handle cavity section 70. The slider $S_2$ is then moved to overlie side handle slot 74 and slider pin 78 inserted. This effectively traps slider $S_2$ between lower end 73 and upper end 75 of side handle slot 74. Slider $S_2$ cannot work free of handle $H_2$.

Securing blade $B_2$ interior of blade securing cavity 50 is straightforward. Blade $B_2$ is placed interior of blade securing cavity 50 and pin P utilized to secure the blade. Mating engagement of cavity side edge 52 and cavity upper edge 54 with respective blade side edge 62 and blade upper edge 64 completes the assembly.

It now remains to understand the construction of pin P and the interior of slider $S_2$ at blade cavity section 72. This can be best done with respect to FIG. 4A and 4B.

Referring to FIG. 4A, blade $B_2$ is shown folded at hinge G so that the blade $B_2$ is parallel to a side of handle $H_2$. A section is taken so that the inside construction of slider $S_2$ at cavity $C_2$ within blade cavity section 72 can be set forth. This section is shown in FIG. 4B.

In the inside wall 81 of slider $S_2$ there is provided a release detent cavity 94 and a locking detent aperture 92. At the same time it will be noticed that pin P includes two separate sections. Pin P includes a pin body 80 having a head 82 shaped as a frustrum. It will also be observed that locking detent aperture 92 shares the frustrum profile, the pin head 82 having the male profile and the locking detent aperture 92 having the female profile.

Having set forth this much, operation can now be described. When the scalpel is shipped, hinge G is folded to the configuration set forth in FIG. 4A. Blade $B_2$ folds back parallel to handle $H_2$. Slider $S_2$ is moved downward so that release detent cavity 94 fits over pin head 82. It is held in this position during shipping.

When use is desired, slider $S_2$ is moved upward. release detent cavity 94 releases and blade $B_2$ is folded in alignment with the major portion of handle $H_2$. Thereafter, slider $S_2$ is moved downward over hinge G, locking hinge G in the extended position. Use of the scalpel occurs.

For disposal, slider $S_2$ is again moved upward. Thereafter, the scalpel is folded at hinge G to the disposition shown in FIG. 4A. Thereafter, slider $S_2$ moves downward over blade $B_2$. This time movement continues until locking detent aperture 92 keys to pin head 82. In this disposition, permanent locking occurs. This permanently locked position is specifically illustrated in the side elevation section of FIG. 4B.

Figure 5:
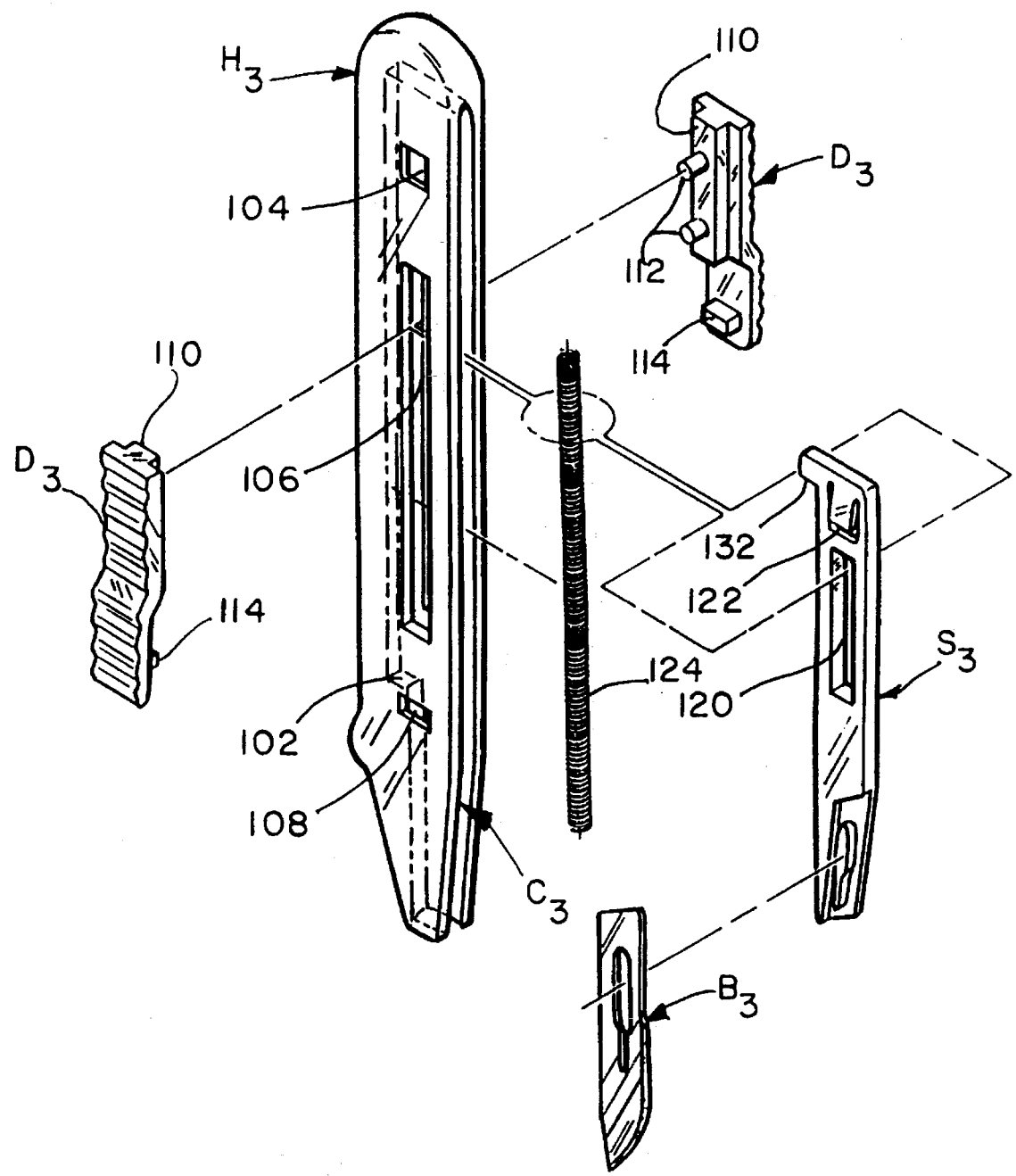
FIG. 5 is an exploded isometric view of a third scalpel embodiment in which a spring biased blade holder and blade normally bias the scalpel blade interior of the handle and provision is made both for surgeon grasping of the scalpel to hold the scalpel blade in a cutting disposition as well as providing for permanent one-way scalpel retraction to permanent retracted position upon completion of scalpel use.
Figures 6A, 6B:
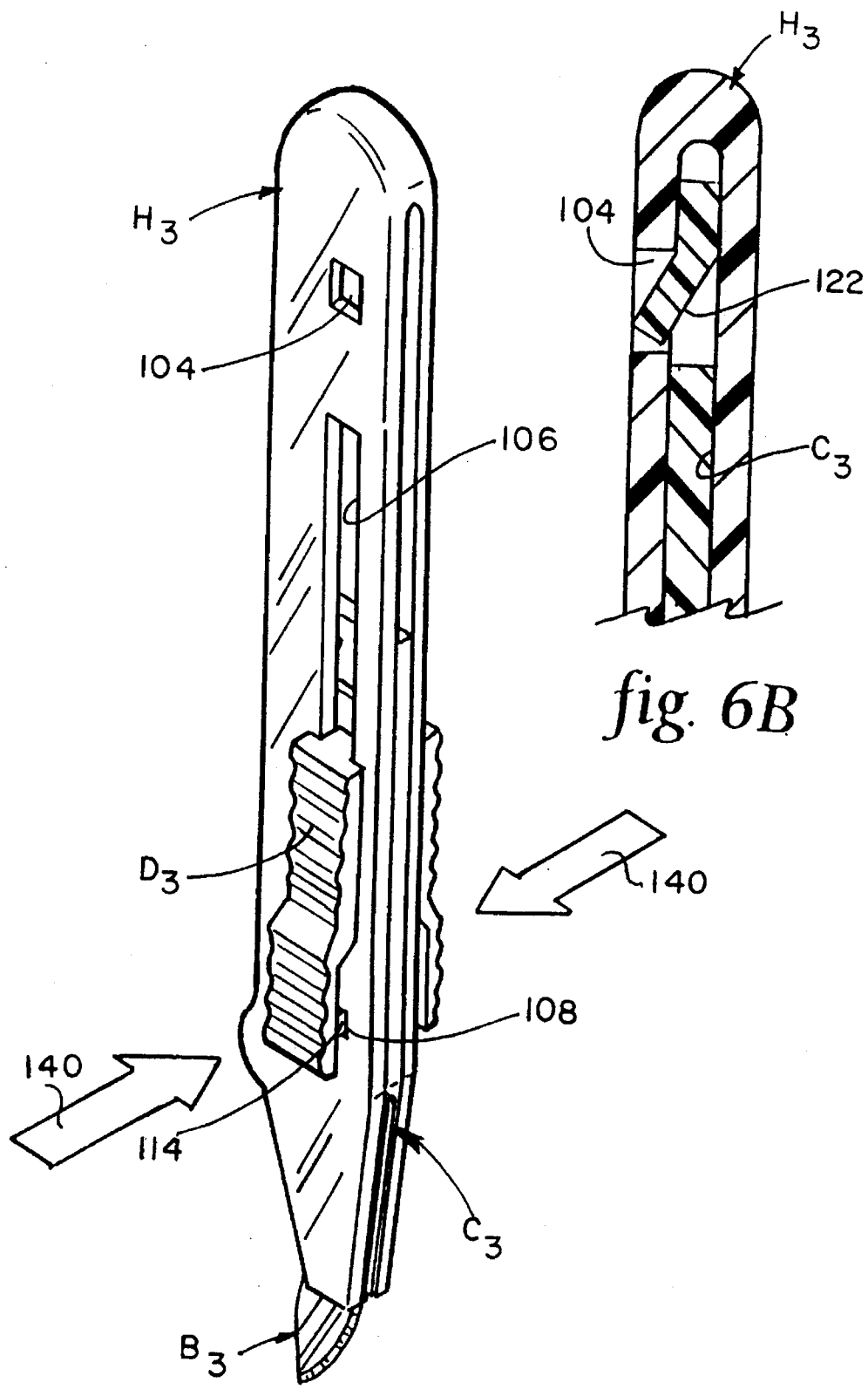
FIG. 6A and 6B are respective details of the scalpel of FIG. 5 with FIG. 6A illustrating the scalpel held in the blade exposing disposition during surgery and FIG. 6B illustrating the scalpel permanently retracted into the handle for disposal.

Having set forth the second embodiment, the third embodiment related to FIGS. 5, 6A and 6B can now be set forth.

Referring to the isometric view of FIG. 5, handle $H_3$ is illustrated having an internal cavity $C_3$. This handle $H_3$ includes an interior spring notch 102, a locking detent window 104, a moving latch window 106, and a blade extension window 108. Locking detent window 104 only is configured in one side of handle $H_3$; moving latch windows 106 and blade extension windows 108 are on both sides of handle $H_3$.

A slider $S_3$ is provided. Likewise, a blade $B_3$ is provided. In a manner precisely analogous to the construction illustrated in FIG. 1, slider $S_3$ has blade $B_3$ secured to the slider $S_3$ once placement occurs within cavity $C_3$ of handle $H_3$. Such construction detail will not be repeated here.

Detent $D_3$ includes paired halves. Each half includes detent slides 110 with detent pins 112 in one half engaging apertures (not shown) in the opposite half. At the bottom of detent $D_3$, there is provided an extension grasper 114. It will be seen that extension grasper 114 enables detent $D_3$ to hold blade $B_3$ in the extended position during use of the scalpel.

Slider $S_3$ includes a detent aperture 120. It differs from the preceding construction of FIG. 1 in the inclusion of a detent stop 122 and a spring stop 132.

Finally, there is included a compression spring 124. As will here in after be more fully understood, it is the purpose of compression spring 124 to bias slider $S_3$ and blade $B_3$ interior of cavity $C_3$ of handle $H_3$.

Having set forth the general construction, assembly can now be set forth. This is best done with simultaneous reference to FIGS. 5 and 6A.

Blade $B_3$ is assembled to slider $S_3$. Thereafter, placement of slider $S_3$ occurs within cavity $C_3$. As in the case of the embodiment illustrated in FIG. 1, trapping of blade $B_3$ to slider $S_3$ occurs.

The insertion of slider $S_3$ occurs with one important exception. Specifically, compression spring 124 also must be assembled at this time. Specifically, one end of compression spring 124 is placed at spring notch 102 interior of cavity $C_3$. The remaining end of compression spring 124 is placed against spring stop 132 in slider $S_3$. When slider $S_3$ is fully within cavity $C_3$, compression spring 124 is trapped interior of cavity $C_3$ under compression with the side of slider $S_3$ trapping the compression spring on one side and the side of cavity $C_3$ trapping the compression spring on the remaining three sides.

Assuming that compression spring 124 and slider $S_3$ are in place, detent $D_3$ is then assembled. Specifically, detent slides 110 ride interiorly of moving latch window 106. Further, detent pins 112 connect the respective detent halves across detent aperture 120 in slider $S_3$. This completes the assembly of the scalpel.

At this juncture it will be observed that compression spring 124 normally biases blade $B_3$ into cavity $C_3$. Left alone, blade $B_3$ will be retracted by the compression expansion of compression spring 124 to retract the blade into a sharp-safe disposition interior of handle $H_3$.

Disposition of blade $B_3$ for use is easily understood. Specifically, extension graspers 114 of detent $D_3$ are flexibly mounted with respect to detent $D_3$. Assuming that a surgeon moves detent $D_3$ forward against the compression of compression spring 124, blade $B_3$ will protrude outwardly of handle $H_3$. When protruding outwardly of handle $H_3$, extension graspers 114 can register overlying blade extension windows 108. Presuming that a surgeon presses inwardly on detent $D_3$ at the location indicated by arrows 140, extension graspers 114 can penetrate into blade extension windows 108. So long as this force is maintained, a positive extension of blade $B_3$ will occur; once this force is released, immediate retraction of blade $B_3$ will occur. Thus it will be understood that any time the scalpel is let out of the hand of the surgeon, immediate retraction of blade $B_3$ will occur into handle $H_3$.

There remains only the locked, sharp-safe disposition at the end of surgery.

Referring to FIG. 5 and 6B, this sharp-safe disposition can be fully understood. Referring to FIG. 5, slider $S_3$ is provided with a detent stop 122. Detent stop 122 is conventionally manufactured by molding a U-shaped aperture at the top of slider $S_3$ and having the mold deform the interior tab defined by the "U" to one side, to be engageable with locking detent window 104. This bent interior tab serves two functions.

First, and assuming normal retraction of blade $B_3$ and slider $S_3$, detent stop 122 will inhibit full retraction of slider $S_3$ into cavity $C_3$. The force of compression spring 124 will not be sufficient to bias detent stop 122 to engage locking detent window 104.

Second, and when surgery is completed, the surgeon can overcome detent stop 122 and force the detent interior of locking detent window 104. Detent stop 122 will engage the edge of the locking detent window 104. Further, this engagement will be for all effective purpose a one-way engagement that will not be capable of convenient reversal. Thus, blade $B_3$ will be locked in a sharp-safe disposition interior of handle $H_3$.

Figures 7, 8A, 8B:
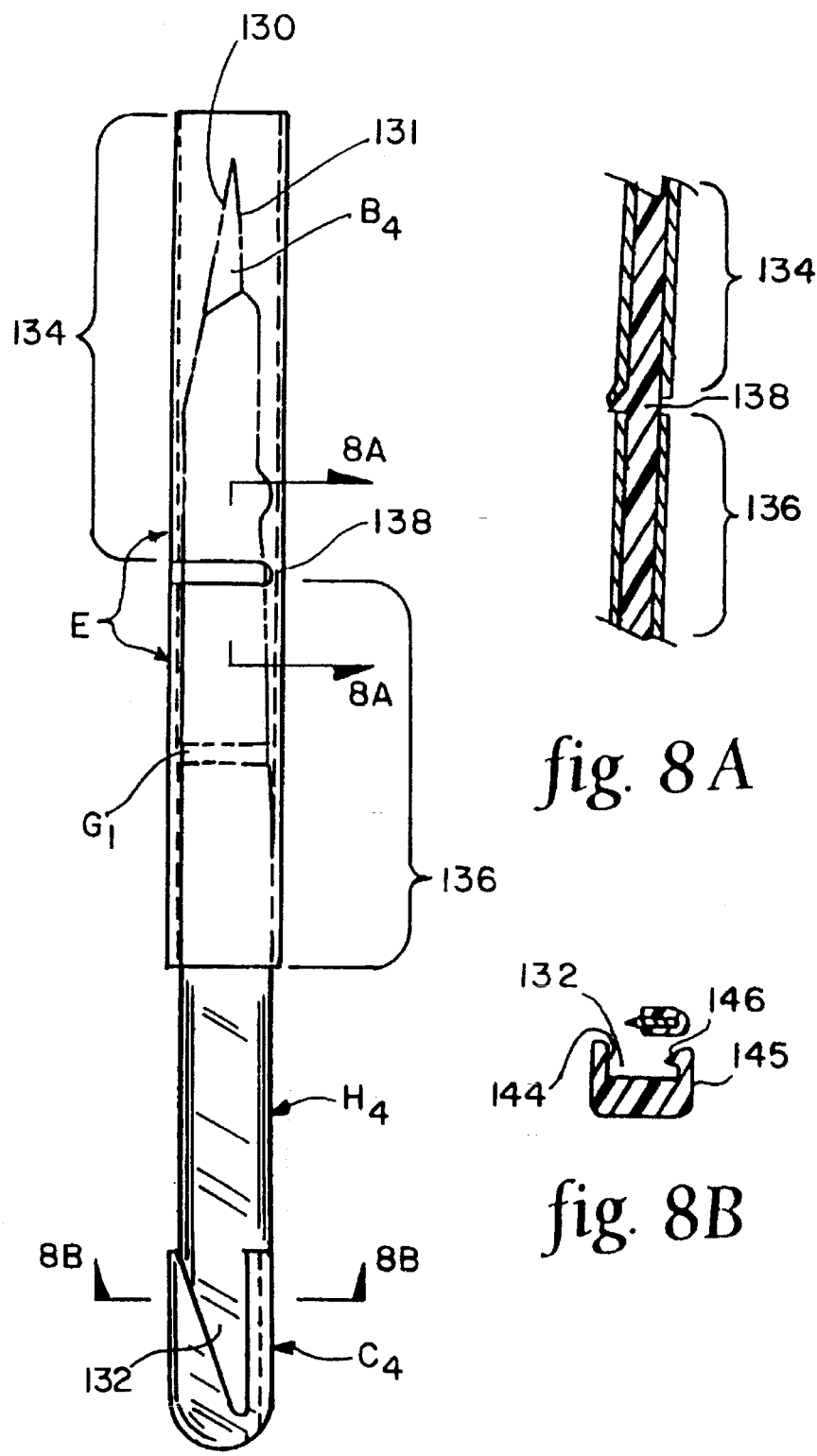
FIG. 7 is a side elevation of an additional embodiment illustrating in side elevation a scalpel with a removable blade covering sheath having a hinge in the plane of the handle with provision for folding the scalpel after use and capturing the blade within a latch integral to the handle; and, FIGS. 8A and 8B are respective details at the removable sheath and at the blade receiving latch.

Referring to FIG. 7, 8A and 8B an alternative embodiment is disclosed. A scalpel having a handle $H_4$ is illustrated covered by a sheath E. Sheath E has a removable sheath section 134, a slidable sheath section 136, and a break away sheath section 138.

Sheath E has a friction fit over scalpel handle $H_4$. The sheath E is sufficiently tight with respect to the handle that it may slide under force relative to the handle.

Removable sheath section 134 covers blade $B_4$ with cutting edge 130. Slidable sheath section 136 extends across a hinge $G_1$ in the plane of handle $H_4$. The construction of hinge $G_1$ is precisely analogous to that hinge G previously illustrated with respect to FIG. 3. When this type of hinge is covered with the semi-rigid membrane of sheath E, the hinge remains in the extended or straight disposition during scalpel use.

Handle $H_4$ includes at the distal end a cavity $C_4$. Cavity $C_4$ has a blade receiving opening 132. Blade receiving opening 132 has a side elevation profile approximately equivalent to—but a little smaller than—the side elevation profile of blade $B_4$ and the portion of the handle $H_4$ immediate to blade $B_4$. Three observations can be made about cavity $C_4$.

First, cavity $C_4$ is spaced from hinge $G_1$ a distance so that when handle $H_4$ is bent in the major plane of the handle, blade $B_4$ registers to the blade shaped profile of cavity $C_4$.

Second, cavity $C_4$ defines a straight side wall 144 which can capture cutting edge 130. Thus the cutting edge 130 will pass even with side wall 144 and will be held in close registration with respect to the side wall 144.

Third, catch wall 145 is provided with capturing ledge 146. Thus, when blade $B_4$ at non sharpened edge 131 passes adjacent capturing ledge 146 in catch wall 145, it snaps into and is held in place within blade receiving opening 132.

Assembly is easily understood. Handle $H_4$ and blade $B_4$ are assembled as a unit. Thereafter, sheath E with sections 134 and 136 joined by break away section 138 are slipped over handle $H_4$ and blade $B_4$. Thereafter, the unit is packaged and shipped.

Use is likewise easily understood. Scalpel handle $H_4$ is grasped at sliding sheath 136. Removable sheath 134 is likewise grasped and pulled away from sliding sheath 136 so as to sever break away sheath section 138. This exposes blade $B_4$. At the same time, sliding sheath section 136 maintains hinge $G_1$ in the extended disposition. Use of the scalpel occurs.

When the scalpel is through being used, sliding sheath section 136 is moved toward cavity $C_4$ a sufficient distance to clear hinge G₁. Upon clearing the hinge G₁, folding of handle H₄ occurs about hinge G₁ until blade B₄ registers with cavity C₄. Such folding can occur by the surgeon grasping handle H₄ and folding blade B₄ against a hard metal surfaced such as a table in the operating room. Pressing of blade B₄ will continue until snapping of the blade into cavity C₄ occurs—giving a tactile indication of the sharp-safe disposition of the blade. Thereafter, safe discard may occur.

It will be understood that this final design with the severable sheath E is similar to existing scalpels. The hinge G₁, the sliding sheath section 136, and the snap receiving cavity C₄ constitute the added features for enabling the sharp-safe disposal of this invention.

What is claimed is:

1. A disposable scalpel comprising:

a scalpel handle defining a first side and a second side;

a scalpel blade;

means securing said scalpel blade to said scalpel handle including;

a body coupled to said handle, said body permitting movement of said scalpel blade relative to said scalpel handle, and a detent member slidably engaged with said scalpel handle, said detent member exposed for manipulation relative to said scalpel handle from said first side and said second side of said scalpel handle;

first means for disposing said scalpel blade with respect to said scalpel handle between a scalpel storage position where said scalpel blade is covered and a scalpel use position where said scalpel blade is exposed for cutting, said first means including at least one detent on said detent member for co-action with at least one detent member attached to said scalpel handle; and second means for one-way moving and maintaining said scalpel blade with respect to said scalpel handle from said scalpel use position to a stowed disposition with said blade permanently covered whereby said scalpel can be discarded, said second means including a detent on said detent member for co-action with a detent member attached to said handle.

2. The disposable scalpel of claim 1 and further including:

said first and second sides having a defined interval therebetween for receiving a scalpel blade and an opening at one end for permitting a blade to move into and out of a blade exposed cutting position with respect to said handle;

said scalpel handle further defining a central slot for receiving a blade mounted detent, said central slot exposing a blade mounted detent through said first side and said second side for manipulation against first and second detent members defined in said central slot;

said means securing said scalpel blade to said scalpel handle further including a key on said body and a keyway on said scalpel blade for securing said blade to said body, said body permitting reciprocal movement of said blade into and out of said scalpel handle;

said first means including first and second releasable detents on said detent member for co-action with respect to said first and second detent members on said slot; and, said second means including a second detent for permanently engaging one of said detents defined on said slot.

3. A disposable scalpel comprising:

a scalpel handle, said handle defining first and second sides with a defined interval therebetween for receiving a scalpel blade and an opening at one end for permitting a blade to move into and out of a blade exposed cutting position with respect to said handle;

said scalpel handle defining a central slot for receiving a blade mounted detent, said central slot exposing a blade mounted detent for manipulation against first and second detent members defined in said central slot, said central slot exposing a blade mounted detent for manipulation from the first and second sides;

a scalpel blade;

a detent member for mounting to said blade at said central slot for imparting sliding movement of said detent member within said slot to reciprocation of said blade within said handle including movement to and from a blade exposed cutting position of said scalpel blade;

means securing said scalpel blade to said scalpel handle, said means including a body for permitting reciprocal movement of said blade into and out of said scalpel handle;

first means for disposing said scalpel blade with respect to said scalpel handle between a scalpel storage position where said scalpel blade is covered and a scalpel use position where said scalpel blade is exposed for cutting, said first means including first and second releasable detents on said detent member for co-action with respect to said first and second detent members on said slot; and, second means for one-way moving and maintaining said scalpel blade with respect to said scalpel handle from said scalpel use position to a stowed disposition with said blade covered permanently covered, said second means including a second detent for permanently said detent member to one of said detents defined on said slot whereby said scalpel can be discarded with said blade of said scalpel permanently within said handle.

4. The disposable scalpel of claim 3 and wherein:

said first and second detents are affixed to said handle and one of said detents has a dimension greater than the other of said detents.

5. A disposable scalpel comprising:

a scalpel handle, said handle defining first and second sides with a defined interval therebetween for receiving a scalpel blade and an opening at one end for permitting a blade to move into and out of a blade exposed cutting position with respect to said handle;

said scalpel handle defining a central slot for receiving a blade mounted detent, said central slot exposing a blade mounted detent for manipulation against first and second detent members defined in said central slot;

a scalpel blade;

a detent member for mounting to said blade at said central slot for imparting sliding movement of said detent member within said slot to reciprocation of said blade within said handle including movement to and from a blade exposed cutting position of said scalpel blade;

means securing said scalpel blade to said scalpel handle, said means including a body for permitting reciprocal movement of said blade into and out of said scalpel handle;

first means for disposing said scalpel blade with respect to said scalpel handle between a scalpel storage position where said scalpel blade is covered and a scalpel use position where said scalpel blade is exposed for cutting, said first means including first and second releasable detents on said detent member for co-action with respect to said first and Second detent members on said slot; and second means for one-way moving and maintaining said scalpel blade with respect to said scalpel handle from said scalpel use position to a stowed disposition with said blade covered permanently covered, said second means including a second detent for permanently said detent member to one of said detents defined on said slot whereby said scalpel can be discarded with said blade of said scalpel permanently within said handle;

wherein said means for securing said scalpel blade to said scalpel handle includes a key on said body and a keyway on said blade for securing said scalpel blade to said body.

\* \* \* \* \*